(12) United States Patent
Visveshwara

(10) Patent No.: US 9,504,443 B2
(45) Date of Patent: Nov. 29, 2016

(54) SYSTEM AND METHOD FOR MEASURING FLUIDICS IN ARTERIES

(71) Applicant: Nadarasa Visveshwara, Fresno, CA (US)

(72) Inventor: Nadarasa Visveshwara, Fresno, CA (US)

(73) Assignee: Nadarasa Visveshwara, Fresno, CA (US)

( * ) Notice: Subject to any disclaimer, the term of this patent is extended or adjusted under 35 U.S.C. 154(b) by 0 days.

(21) Appl. No.: 14/789,137

(22) Filed: Jul. 1, 2015

(65) Prior Publication Data

US 2016/0007953 A1     Jan. 14, 2016

Related U.S. Application Data

(62) Division of application No. 14/326,034, filed on Jul. 8, 2014, now Pat. No. 9,320,493.

(51) Int. Cl.
*A61B 8/12* (2006.01)
*A61B 8/06* (2006.01)
(Continued)

(52) U.S. Cl.
CPC ............ *A61B 8/12* (2013.01); *A61B 5/021* (2013.01); *A61B 5/0205* (2013.01); *A61B 5/150038* (2013.01); *A61B 5/4839* (2013.01); *A61B 8/06* (2013.01); *A61B 8/065* (2013.01); *A61B 8/0866* (2013.01); *A61B 8/445* (2013.01); *A61B 8/4477* (2013.01); *A61B 8/488* (2013.01); *A61B 8/0891* (2013.01); *A61B 8/4416* (2013.01); *A61B 8/4483* (2013.01); *A61B 8/5223* (2013.01); *A61B 2503/045* (2013.01)

(58) Field of Classification Search
CPC ............ A61B 8/12; A61B 8/02; A61B 8/06; A61B 8/445; A61B 8/4483; A61B 8/461; A61B 8/488; A61B 5/0205; A61B 5/021; A61B 5/150038; A61B 5/4839
See application file for complete search history.

(56) References Cited

U.S. PATENT DOCUMENTS

| | | | |
|---|---|---|---|
| 4,665,925 A | 5/1987 | Millar | |
| 4,915,103 A | 4/1990 | Visveshawara et al. | |

(Continued)

FOREIGN PATENT DOCUMENTS

EP     0 253 687 A2     1/1988

OTHER PUBLICATIONS

Final Office Action issued in U.S. Appl. No. 14/326,034, mailed on Aug. 20, 2015, 21 pages.
(Continued)

*Primary Examiner* — Bo J Peng
(74) *Attorney, Agent, or Firm* — Davis Wright Tremaine LLP; Philip H. Albert

(57) ABSTRACT

An apparatus for performing measurements in an artery includes a Doppler catheter, comprising a Doppler transducer and a wire connected to the Doppler transducer; and an elongated catheter body having a conduit therein for housing the wire of the Doppler catheter. The body has a proximal end and a distal end; wherein the wire is movable in the conduit relative to the catheter body so that the Doppler transducer and the wire are capable of being threaded into said conduit at the proximal end after the distal end of the catheter has been inserted into the artery, until the Doppler transducer emerges outside the conduit at the distal end of said body for performing ultrasound measurements in the artery. Another embodiment employs at least an additional side transducer for measuring the cross-sectional dimension of the artery useful for computing blood flow.

20 Claims, 9 Drawing Sheets

(51) Int. Cl.
*A61B 8/08* (2006.01)
*A61B 5/00* (2006.01)
*A61B 5/15* (2006.01)
*A61B 8/00* (2006.01)
*A61B 5/021* (2006.01)
*A61B 5/0205* (2006.01)

(56) References Cited

U.S. PATENT DOCUMENTS

| | | | | |
|---|---|---|---|---|
| 5,105,818 | A * | 4/1992 | Christian | A61B 8/06 600/463 |
| 5,121,749 | A * | 6/1992 | Nassi | A61B 5/028 600/465 |
| 5,163,911 | A * | 11/1992 | Sirimanne | A61M 25/01 600/585 |
| 5,176,141 | A * | 1/1993 | Bom | A61B 8/12 600/467 |
| 5,246,007 | A | 9/1993 | Frisbie et al. | |
| 5,405,318 | A | 4/1995 | Nita | |
| 5,433,205 | A * | 7/1995 | Visveshwara | A61B 8/06 600/455 |
| 5,779,643 | A | 7/1998 | Lum et al. | |
| 5,800,395 | A | 9/1998 | Botich et al. | |
| 2001/0045899 | A1 | 11/2001 | Hoek | |
| 2003/0225336 | A1 | 12/2003 | Callister et al. | |
| 2004/0122354 | A1 * | 6/2004 | Semba | A61B 8/06 604/66 |
| 2005/0054982 | A1 * | 3/2005 | Bellucci | A61B 5/1427 604/131 |
| 2012/0078106 | A1 * | 3/2012 | Dentinger | A61B 8/06 600/454 |
| 2014/0276609 | A1 * | 9/2014 | Magee | A61B 19/2203 604/509 |

OTHER PUBLICATIONS

"Ductus Arteriosus," www.wikipedia.com, Jan. 15, 2014, 2 pages.
"Patent Ductus Arteriosus," www.wikipedia.com, Mar. 17, 2014, 6 pages.
"Ventilation/Perfusion Ratio," www.wikipedia.com, Jan. 15, 2014, 3 pages.
"Ventricular Assist Device," www.wikipedia.com, Jul. 3, 2014, 11 pages.
Ahmed et al., "Systolic Time Intervals as Measures of the Contractile State of the Left Ventricular Myocardium in Man," Sep. 1972, Circulation, American Heart Association, vol. XLVI, pp. 559-571.
Cikes et al., "The Shape of the Aortic Outflow Velocity Profile Revisited: Is There a relation Between Its Asymmetry and Ventricular Function in Coronary Artery Disease?" European Journal of Echocardiography, 2009, vol. 10, pp. 847-857.
Livingstone, "Ultrasound-Based Methods of Cardiac Output Monitoring," Chapter 30, Copyright 2000, 1995, 1990, 1985, 1979, 7 pages.
Non-Final Office Action issued in U.S. Appl. No. 14/326,034, mailed on Apr. 17, 2015, XXXX pages.
International Search Report and Written Opinion issued in International Patent Application No. PCT/US2015/037347, mailed Sep. 29, 2015, 10 pages.
Non-Final Office Action issued in U.S. Appl. No. 14/326,034, mailed Dec. 11, 2015, 16 pages.

* cited by examiner

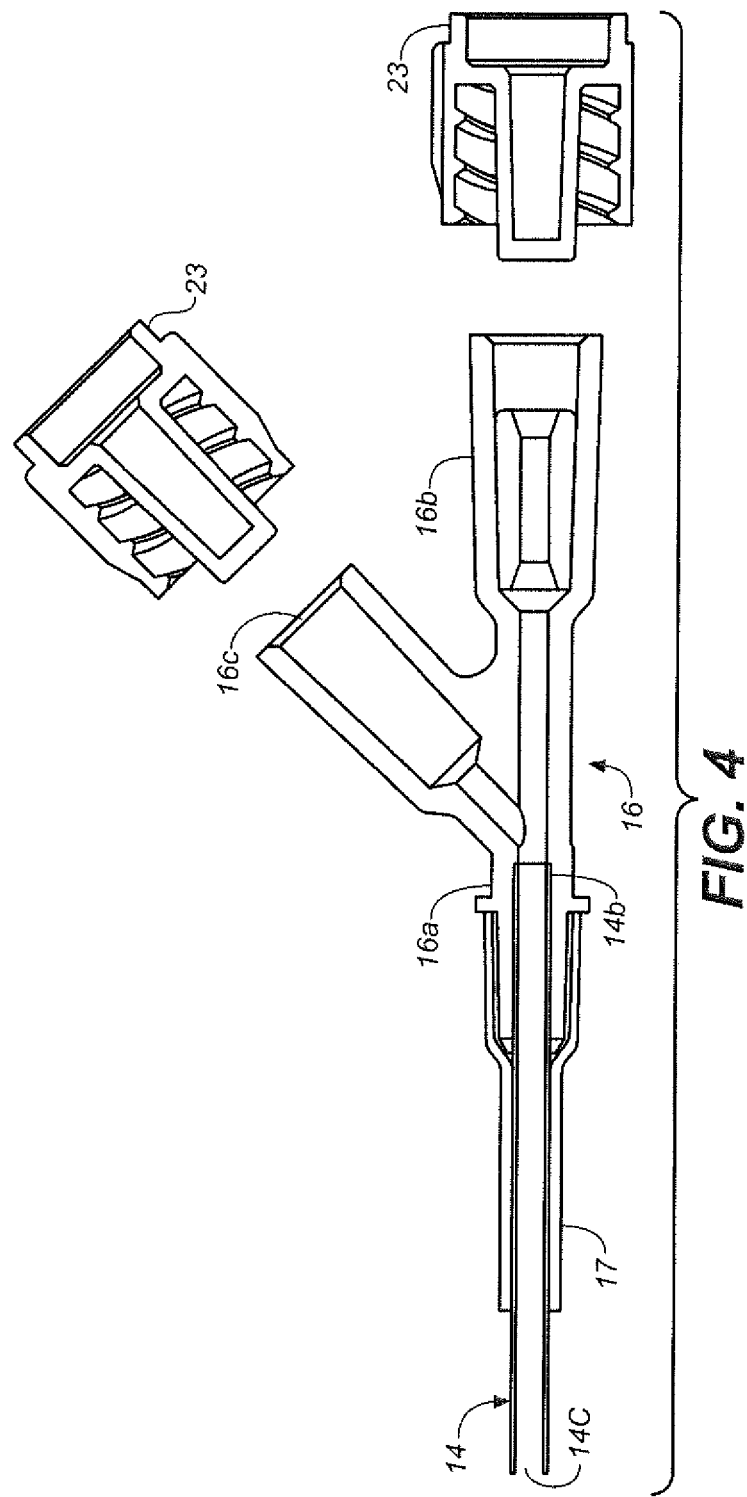

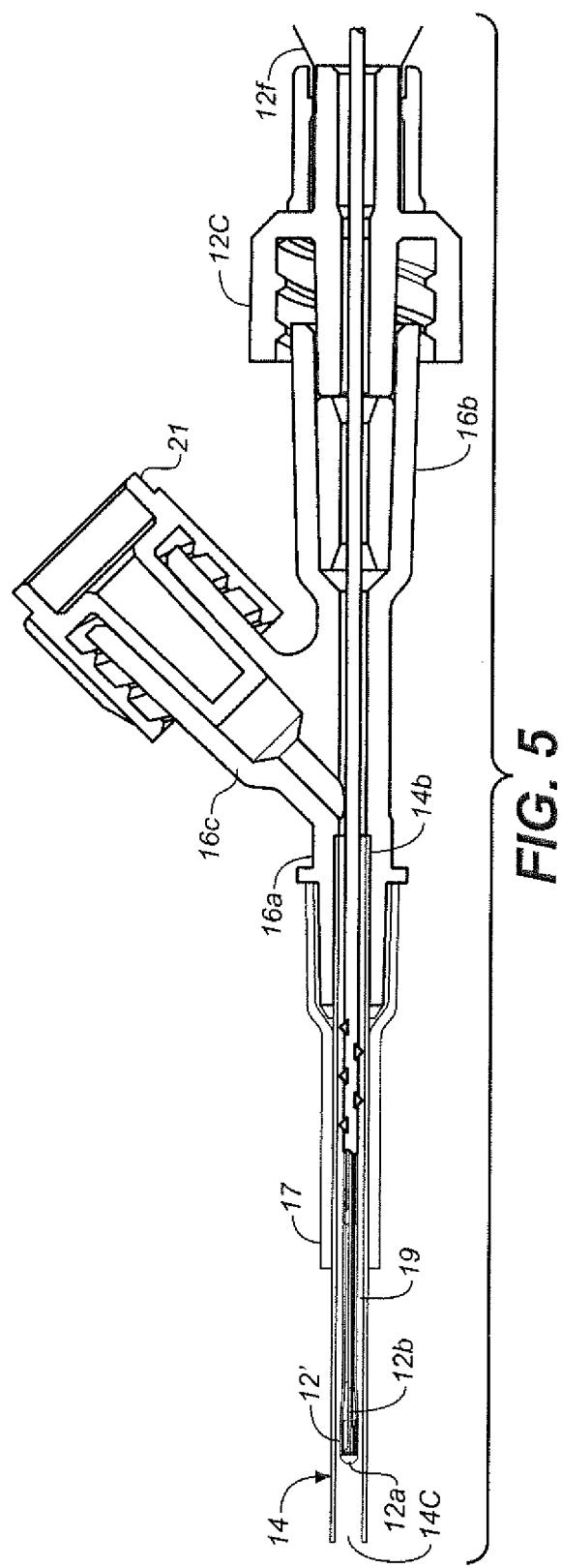

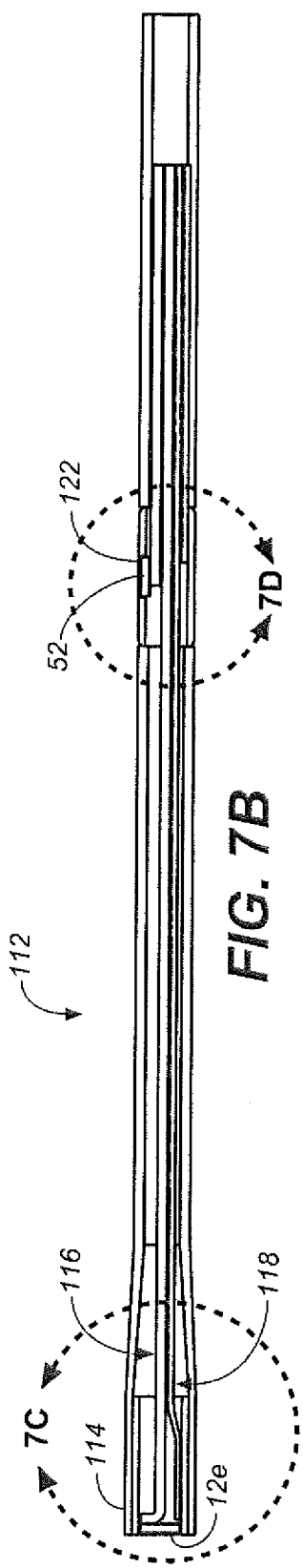
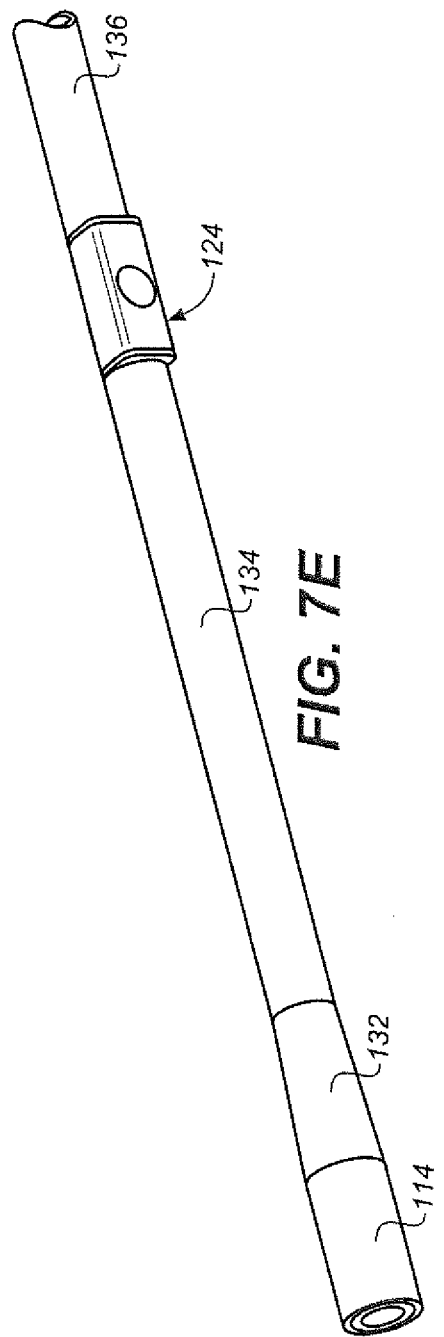

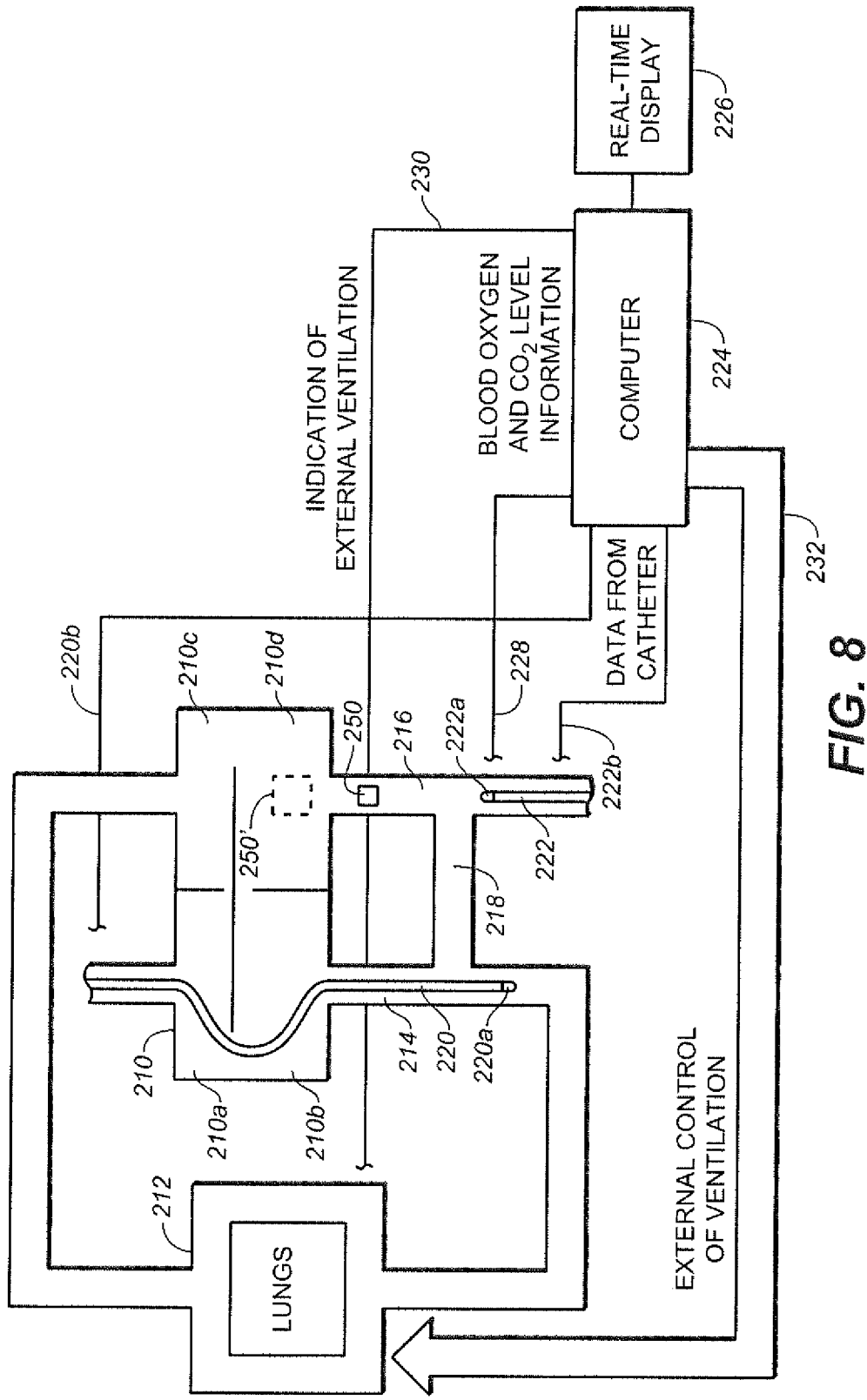

SYSTEM AND METHOD FOR MEASURING FLUIDICS IN ARTERIES

CROSS-RELATED APPLICATION

This application is a divisional of U.S. patent application Ser. No. 14/326,034 filed Jul. 8, 2014, which application is incorporated herein by this reference in its entirety.

BACKGROUND OF THE INVENTION

This invention relates in general to systems and methods for measuring arteries and in particular to systems and methods for measuring parameters related to blood in arteries.

Conventional methods for measuring arterial blood mean velocity include Doppler echocardiography and Cardiac Catheterization. Non Invasive Doppler echocardiography used for measuring blood mean velocity in arteries employs a Doppler transducer outside the arteries to transmit ultrasound to the arteries, and must be conducted so that the sound waves are directed to the arteries at angles not more than about 15 degrees from the direction of blood flow. Otherwise, the blood mean velocity measurement is not accurate. For certain locations of the human body, this may not be practical. Conventional cardiac catheterization cannot provide continuous measurement of cardiac output. It is therefore desirable to provide improved systems and methods for measuring arterial blood mean velocity and cardiac output with related derived indices of cardiac function.

SUMMARY OF THE INVENTION

One embodiment of the invention is directed to an apparatus for performing measurements in an artery, comprising a Doppler catheter, including a Doppler transducer and a wire connected to the Doppler transducer; and an elongated catheter body having a conduit therein for housing the wire of the Doppler catheter. The body has a proximal end and a distal end; wherein the wire is movable in the conduit relative to the catheter body so that the Doppler transducer and the wire are capable of being threaded into said conduit at the proximal end after the distal end of the catheter has been inserted into the artery, until the Doppler transducer emerges outside the conduit at the distal end of said body for performing ultrasound measurements in the artery.

Another embodiment of the invention is directed to a method for measuring blood mean velocity in an artery, comprising inserting into the artery an elongated catheter body having a proximal end and a distal end so that the distal end is located at a desired location in the artery for measuring blood mean velocity, the body defining therein a conduit therein. Thereafter inserted into the conduit at the proximal end of the body is a Doppler catheter that includes a Doppler transducer and a wire connected to the Doppler transducer so that the Doppler transducer passes through and extends outside the conduit to be located at said desired location. Ultrasound measurement of the blood mean velocity in the artery at said desired location using the Doppler transducer is performed.

Yet another embodiment of the invention is directed to an apparatus for performing measurements in an artery, comprising a Doppler catheter which includes a Doppler transducer, a second transducer and wires connected to the Doppler transducer and the second transducer. The Doppler catheter is suitable for being inserted and withdrawn from a conduit in an elongated catheter body having the conduit therein for housing the wire of the Doppler catheter. The body has a proximal end and a distal end; wherein said wires are movable in the conduit relative to the catheter body so that the Doppler transducer, the second transducer and the wires are capable of being threaded into said conduit at the proximal end after the distal end of the catheter has been inserted into the artery, until the Doppler transducer and the second transducer emerge outside the conduit at the distal end of said body for performing ultrasound measurement in and measurement of a cross-sectional dimension of the artery.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

BRIEF DESCRIPTION OF THE DRAWINGS

Identical components are labeled by the same numerals in this document.

FIG. 4 is a cross-sectional view of the Y shaped connector of FIG. 1B and of the proximal end of the artery catheter connected to the Y shaped connector.

FIG. 5 is a cross-sectional view of the Y shaped connector of FIG. 1B and one portion of the Doppler catheter that includes the Doppler transducer, a wire and a portion of a sleeve.

FIG. 7B is a cross-sectional view of components of a portion of a cardiac output Doppler catheter of FIG. 7A after the components are assembled.

FIG. 7E is a perspective view of components of a portion of a cardiac output Doppler catheter of FIG. 7A after the components are assembled.

FIG. 8 is a schematic view of parts of the human body, including the heart and lung. This schematic also shows the positions of Doppler-tipped catheters and shows a computer, which can be used for determining the blood flow in a portion of the body.

Identical components are labeled by the same numerals in this document.

DETAILED DESCRIPTION OF EXEMPLARY EMBODIMENTS

Figure 1:
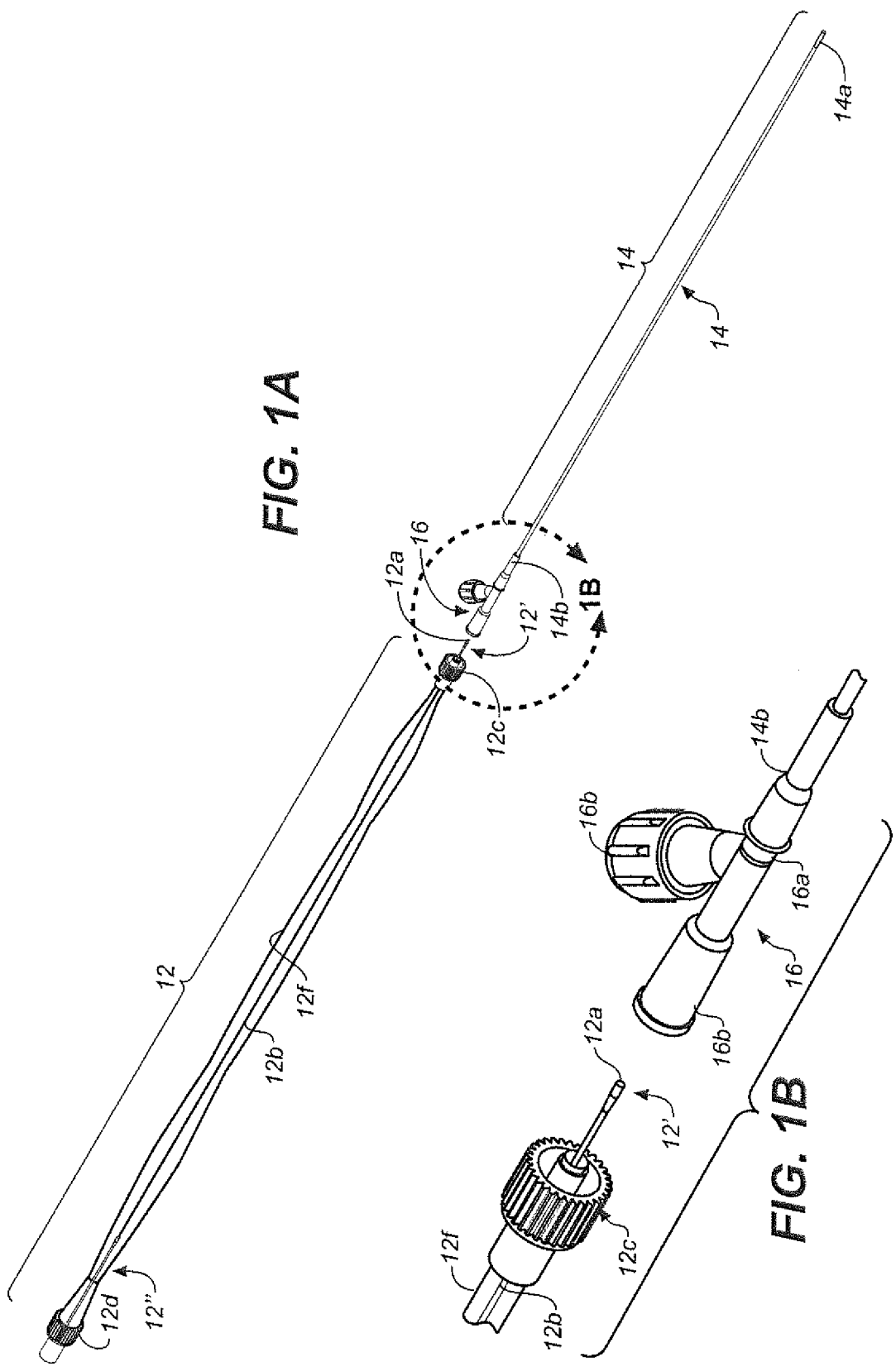
FIG. 1A is a perspective view of a cardiac output Doppler catheter and an artery catheter to illustrate one embodiment of the invention.
FIG. 1B is an exploded view of portions of FIG. 1A within the circle 1B in FIG. 1A.

FIG. 1A is a perspective view of a cardiac output Doppler catheter 12 and an artery catheter 14 to illustrate one embodiment of the invention. FIG. 1B is an exploded perspective view of portions of the apparatus in FIG. 1A within the circle 1B in FIG. 1A. Different from conventional Doppler echocardiography for measuring blood mean velocity which sends ultrasound waves from locations outside the human body, the cardiac output Doppler catheter of FIG. 1A is intended to be placed within an artery. In one application of the embodiment of FIG. 11A, the distal end 14a of an artery catheter 14 is first inserted into an artery (not shown) until its distal end 14a is located at or near a location in the artery desirable for performing ultrasound measurements. Then the distal end 12' of the cardiac output Doppler catheter 12 that contains a Doppler transducer 12a and an electrical wire 12b connected thereto are inserted at the proximal end 14b of the artery catheter into a conduit 14c (see FIGS. 4, 6B) in the body of the artery catheter, where the insertion causes the Doppler transducer 12a and the electrical wire 12b to be moved relative to the conduit until the Doppler transducer 12a exits the distal end 14a of the artery catheter and is located at the desired location in the artery for performing ultrasound measurements.

Figure 2:
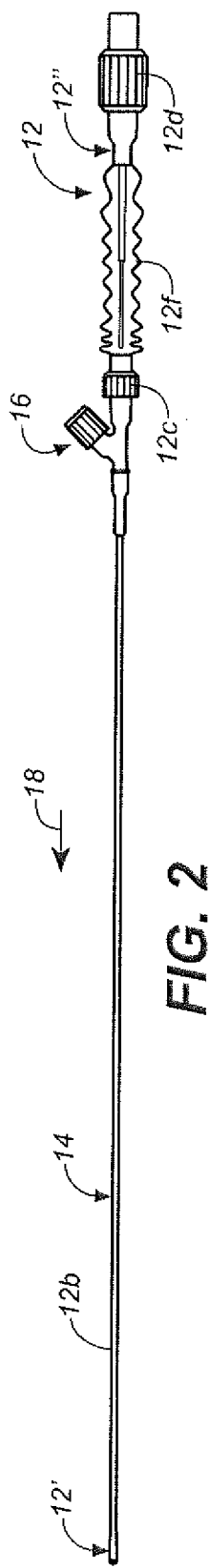
FIG. 2 is a perspective view of the cardiac output Doppler catheter of FIG. 1A where the Doppler transducer extends through a Y shaped connector and inserted into the artery catheter.
Figures 6A, 6B:
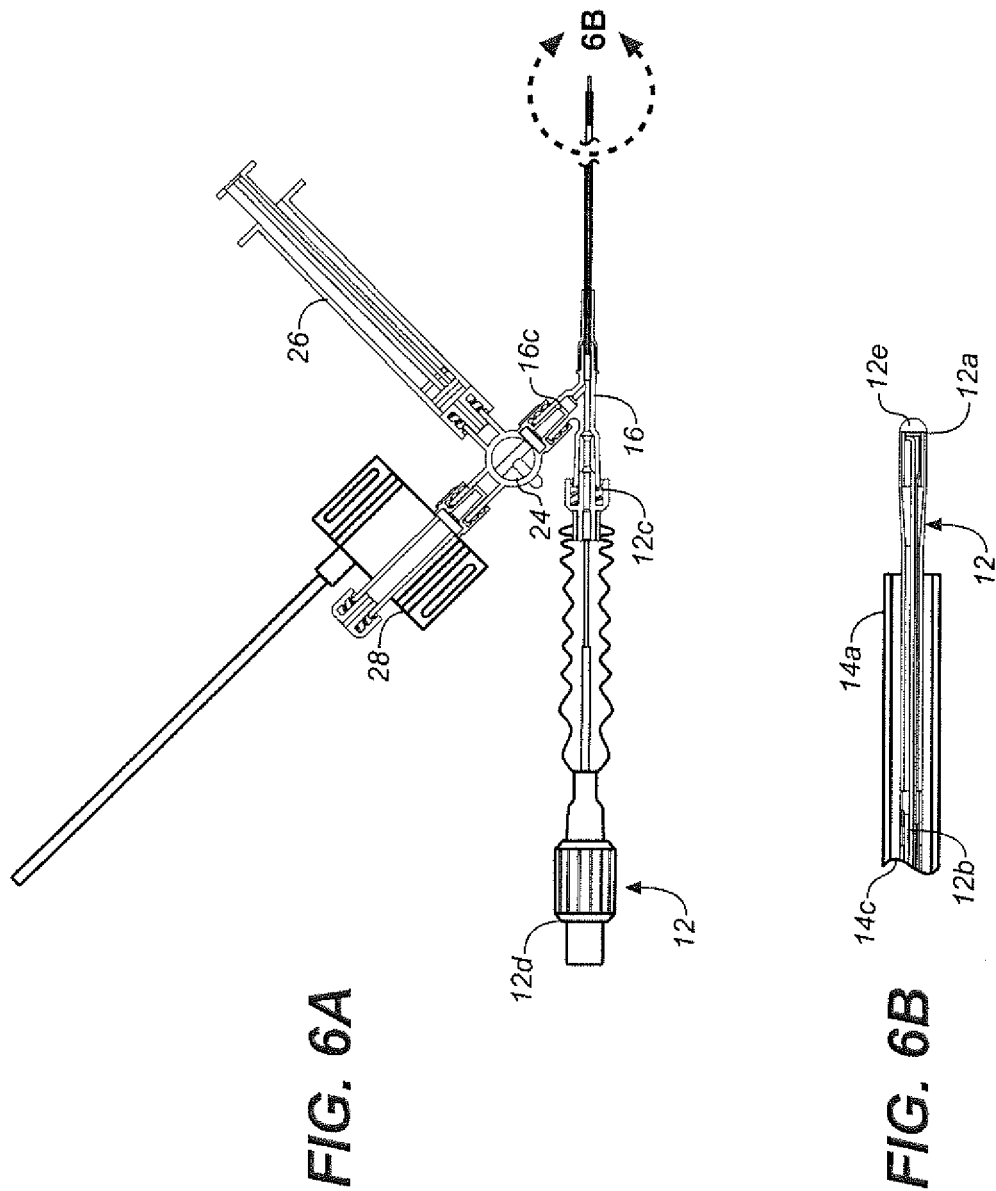
FIG. 6A is a partly perspective and partly cross-sectional view of the cardiac output Doppler catheter and artery catheter of FIG. 1A and a connector with a port connected to a syringe and another port for connection to a pressure transducer to illustrate applications of one embodiment of the invention.
FIG. 6B is an exploded view of a portion of the Doppler catheter and artery catheter of FIG. 6A within the circle 6B in FIG. 6A.

Ultrasound measurements are then performed in a conventional manner using the Doppler transducer 12a. FIG. 2 is a perspective view of the cardiac output Doppler catheter 12 of FIG. 1A where the distal end 12' of the Doppler catheter 12 containing Doppler transducer 12a is inserted through a preferably Y shaped connector 16 into the artery catheter. FIG. 6B shows the relative positions of the Doppler transducer 12a and the distal end 14a of the artery catheter when the Doppler transducer 12a is placed at a position suitable for performing ultrasound measurements in the artery. As shown in FIG. 6B, wire 12b of the cardiac output Doppler catheter 12 is inside the conduit 14c of the artery catheter 14, with a portion of the wire and the Doppler transducer 12a being outside of the conduit 14c to be placed at a location in the artery suitable for performing ultrasound measurement of blood mean velocity. The Doppler transducer 12a is protected by a Doppler tip layer 12e shown more clearly in FIG. 7A.

The advantage of the above arrangement is that since the Doppler transducer 12a is placed in the artery it is measuring, the Doppler transducer can be positioned to send ultrasound waves in a direction substantially parallel to the blood flow and this greatly improves the accuracy of the ultrasound measurement of blood mean velocity in the artery. Another advantage is that continuous measurement of cardiac output can be provided.

As shown in FIGS. 1A and 1B, a first port 16a at the distal end of a Y shaped connector 16 is attached to the artery catheter 14 at the proximal end 14b of the artery catheter. As shown in FIG. 2, the distal end 12' of catheter 12 (containing Doppler transducer 12a) and the wire 12b attached to the transducer are threaded through the Y shaped connector and inserted into a conduit (shown in FIGS. 4 and 6B) within the body of artery catheter 14. As shown in FIGS. 1A and 1B, the cardiac output Doppler catheter 12 includes a connector 12c away from the proximal end 12" of the Doppler catheter 12, and another connector 12d at its proximal end 12'". The cardiac output Doppler catheter 12 also includes a sleeve 12f enclosing and protecting the wire 12b from the environment. The wire 12b is movable relative to connector 12c, so that when the wire is moved from its position substantially all enclosed by sleeve 12f as shown in FIG. 1A to a position as shown in FIG. 2 where most of the wire 12b extends outside the sleeve and is inserted into the conduit of the artery catheter 14, the distal end of the wire 12b (and transducer 12a) is moved past the connector 12c and the Y shaped connector 16 in a forward direction 18. But when the wire 12b is withdrawn from the conduit and moved past the connector 12c back into the sleeve 12f in a direction opposite to direction 18, the distal end of the wire 12b connected to the transducer 12a is then located near the connector 12c as shown in FIG. 1A.

The Y shaped connector 16 has at its proximal end a second port 16b shaped so that the port mates with the connector 12c (shown in FIG. 5) to form a stable and sturdy connection between the artery catheter 14 and the cardiac output Doppler catheter 12. The Doppler transducer 12a in distal end 12' of catheter 12 and the wire 12b are movable relative to port 16a and this stable connection so as to insert or withdraw the Doppler transducer 12a and the wire 12b into or from the conduit in the artery catheter 14.

Figure 3:
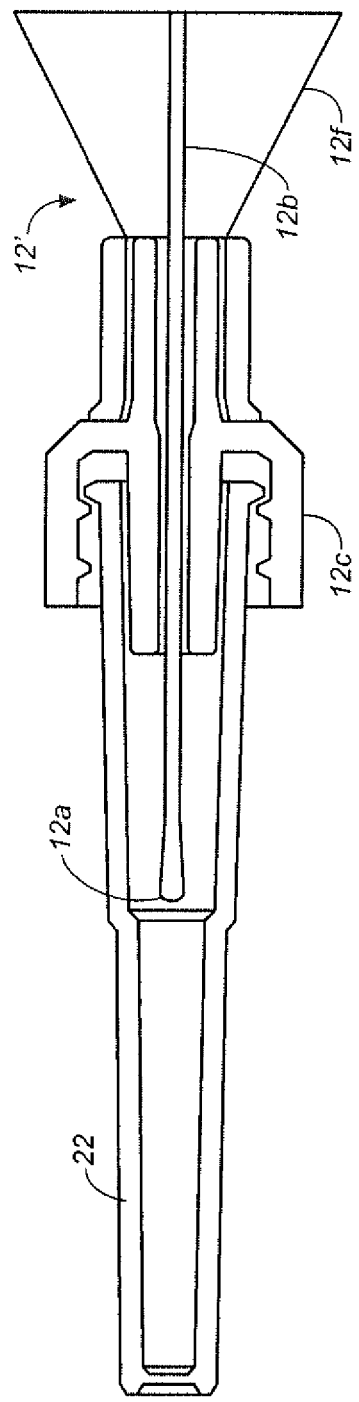
FIG. 3 is a cross-sectional view of one end of the Doppler catheter that includes the Doppler transducer and a cap for protecting the Doppler transducer.

The sleeve 12f is shorter than the wire 12b so that when the wire is withdrawn from the conduit in the artery catheter 14, the sleeve limits the extent by which the wire is withdrawn from the conduit. FIG. 3 is a cross-sectional view of the distal end 12' of the Doppler catheter that contains the Doppler transducer, and of a cap 22 for protecting the Doppler transducer. As shown in FIG. 3, cap 22 is shaped to mate with the connector 12c when the Doppler catheter is not connected to the artery catheter body, to enclose and protect the Doppler transducer 12a. The connector 12c also centers the Doppler transducer 12a when the Doppler transducer is inserted into the conduit in the body of the artery catheter 14.

FIG. 4 is a cross-sectional view of the Y shaped connector of FIG. 1B where the wire 12b of the Doppler catheter 12 is not in the conduit 14c of the artery catheter As shown in FIG. 4, the proximal end 14b of the artery catheter 14 is inserted into the distal end 16a of the Y shaped connector 16, and a shrink tubing 17 fits snugly by a heat shrink process over the connection between the artery catheter 14 and the Y shaped connector 16 to reduce the stress on and chance of breakage of the artery catheter 14. The Y shaped connector 16 includes a Touchy Borst valve that tightens around the Doppler catheter 12 when longitudinal pressure along direction 18 is applied to prevent blood from leaking past and around the Doppler catheter 12 when it is inserted into the conduit of the artery catheter 14.

FIG. 5 is a cross-sectional view of the Y shaped connector of FIG. 1B, the proximal end 14b of artery catheter 14 and a portion of the Doppler catheter 12 that includes the wire 12b and a portion of sleeve 12f, where the wire 12b of the Doppler catheter 12 is in the conduit 14c of the artery catheter 14. As shown in FIG. 5 (not drawn to scale), conduit 14c has cross-sectional dimensions that are such that there is clearance 19 between the Doppler catheter 12 containing wire 12b and the surface of the conduit 14c. This allows a clear path between the third monitoring/infusion port 16*c* (also shown in FIG. 4) of connector 16 and the artery into which the artery catheter is placed, even where wire 12*b* is in the conduit 14*c*. Thus, even where the Doppler catheter 12 has been inserted and is housed by the conduit 14*c*, it is still possible to monitor the blood pressure in the artery through the monitoring/infusion port 16*c* of connector 16 so that the blood pressure of the patient can be monitored while ultrasound measurement of blood mean velocity in the artery is being performed. Of course, where the Doppler catheter 12 is not in the conduit, blood pressure in the artery can be monitored also. The monitoring/infusion port 16*c* of connector 16 can also be used for infusion or injection of a substance such as crystalloids or hyperalimentation fluids. Thus, blood pressure monitoring, substance infusion or injection, and retrieval of blood samples in or from the artery can also be performed while blood mean velocity is being measured as described above, or when the Doppler catheter is not used for measuring blood mean velocity and wire 12*b* is not in conduit 14*c*. These functions may be performed by connecting the appropriate equipment to monitoring/infusion port 16*c* through a port connector 21 that connects to and fits over port 16*c* as shown in FIG. 5. When not in use, port 16*c* and the port at the proximal end 16*b* of the Y shaped connector 16 may be enclosed by means of connectors 23 as shown in FIG. 4.

Preferably, the elongated catheter body of the artery catheter 14 comprises a material firm enough to enable the body to be inserted into arteries, but flexible enough to bend along turns in the arteries, such as turns in an umbilical artery in newborns. In one embodiment, the elongated catheter body of the artery catheter 14 comprises a polyurethane material. While connector 16 preferably is Y-shaped, it will be understood that connector 16 may be in shapes other than Y; such variations are within the scope of the invention. Preferably the monitoring/infusion port 16*c* of connector 16 is located between ports 16*a* and 16*b* at the distal and proximal ends of the connector respectively.

FIG. 6A is a partly perspective and partly cross-sectional view of the cardiac output Doppler catheter 12 and artery catheter 14 of FIG. 1A and of a connector 16 with the monitoring/infusion port 16*c* port connected to yet another connector 24 with two ports: a port connected to a syringe 26 and another port connected to a pressure transducer 28 to illustrate applications of one embodiment of the invention. The connector 24 contains a valve (not shown) therein to allow either the syringe 26 or the pressure transducer 28, but not both, to be connected to port 16*c* at any one time. Part of the cardiac output Doppler catheter 12 is truncated and not shown in FIG. 6A. FIG. 6B is an exploded view of a portion of the Doppler catheter and artery catheter of FIG. 6A within the circle 6B in FIG. 6A. As shown in FIG. 6A, through connectors 16 and 24, the blood pressure in the artery may be monitored by means of a pressure transducer 28 providing a pressure reading at an output. Substances may also be injected into the artery through connectors 16 and 24 by means of syringe 26.

Figure 7A:
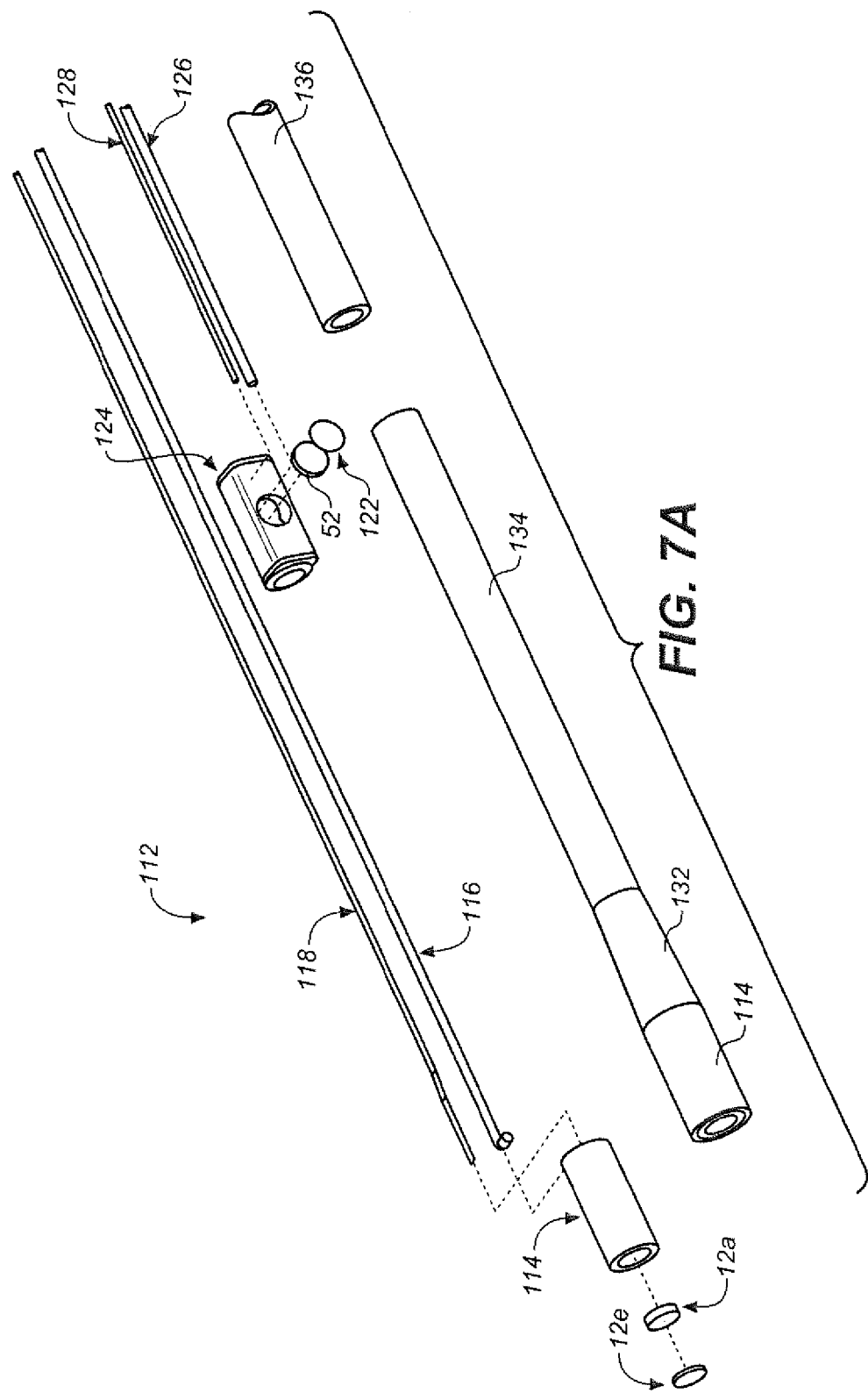
FIG. 7A is a perspective view of components of a portion of a cardiac output Doppler catheter to illustrate an alternative embodiment of the invention with two transducers.
Figure 7C:
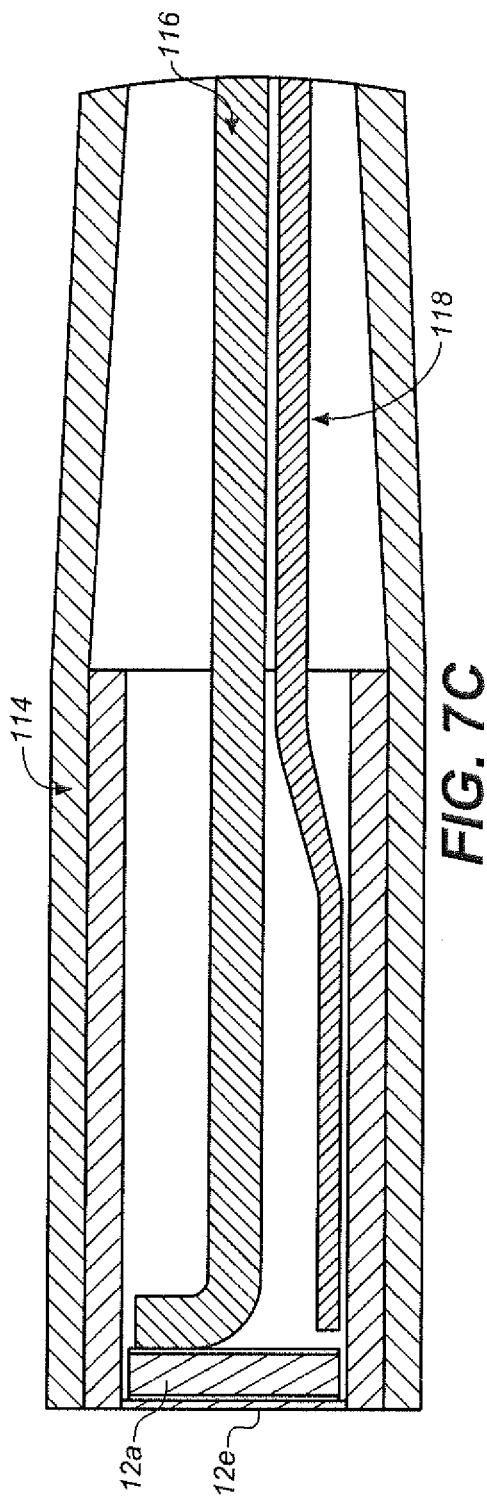
FIG. 7C is a cross-sectional view of a portion of the cardiac output Doppler catheter of FIG. 7A, 7B within the circle 7C in FIG. 7B to illustrate the connections of power and ground leads to the Doppler transducer.
Figure 7D:
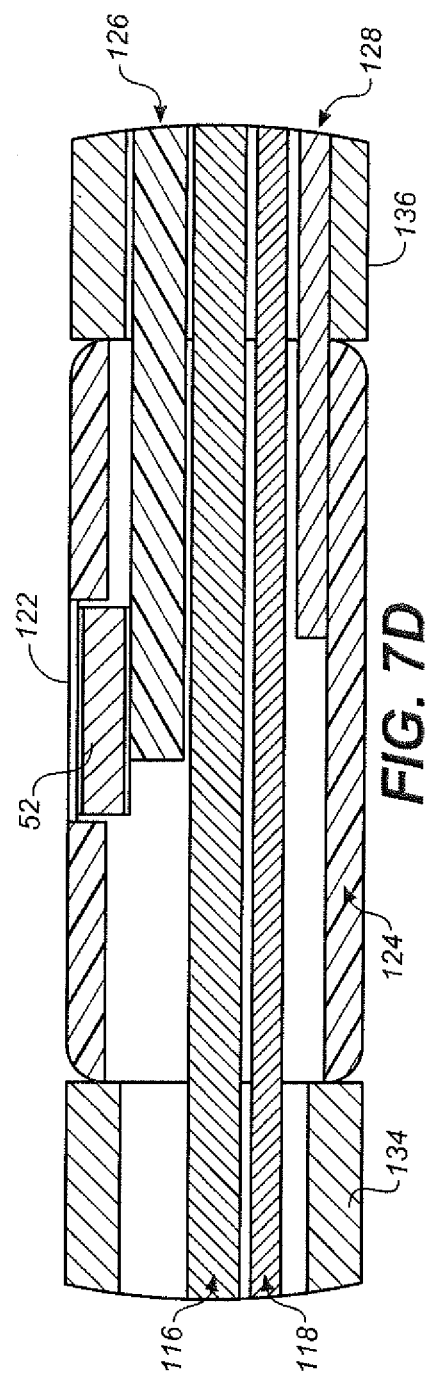
FIG. 7D is a cross-sectional view of a portion of the cardiac output Doppler catheter of FIGS. 7A, 7B within the circle 7D in FIG. 7B to illustrate the connections of power and ground leads to the transducer.

FIG. 7A is a perspective view of components of a portion of a cardiac output Doppler catheter 112 to illustrate an alternative embodiment of the invention with two transducers. FIG. 7B is a cross-sectional view of components of the distal end of the cardiac output Doppler catheter of FIG. 7A after the components are assembled. FIGS. 7C, 7D are cross-sectional views of portions of the cardiac output Doppler catheter of FIGS. 7A, 7B to illustrate the connections of power and ground leads to the two transducers.

As shown in FIG. 7AE instead of having only one Doppler transducer 12*a* as in the embodiments described above, cardiac output Doppler catheter 112 of FIGS. 7A-7E includes at least two transducers: Doppler transducer 12*a* as in the embodiments described above, but also at least a second transducer 52. Transducers 12*a*, 52 comprise piezo crystals #1 and #2 respectively as shown in FIG. 7A. Cardiac output Doppler catheter 112 includes a housing 114 for the piezo crystal #1, which is protected by the housing 114 and a matching layer 12*e* from the environment in the artery. Power lead 116 is electrically connected to piezo crystal #1, and an optional ground lead 118 is preferably electrically connected to housing 114 (connections shown in dashed lines in FIG. 7A). Cardiac output Doppler catheter 112 also includes a housing 124 for the piezo crystal #2, which is protected by the housing 124 and a matching layer 122 from the environment in the artery. Power lead 126 is electrically connected to piezo crystal #2, and an optional ground lead 128 is preferably electrically connected to housing 124 (connections shown in dashed lines in FIG. 7A). The housings 114 and 124 are then connected together by sections 132, 134 of a jacket 1 and section 136 of jacket 2 to form the distal end of cardiac output Doppler catheter 112, where the leads 116, 128, 126, 128 are housed within the sections. FIG. 7B is a cross-sectional view of components of the distal end of the cardiac output Doppler catheter 112 of FIG. 7A after the components are assembled.

FIG. 7C is a cross-sectional view of a portion of the cardiac output Doppler catheter of FIG. 7A, 7B within the circle 7C in FIG. 7B to illustrate the connections of power and ground leads to the Doppler transducer 12*a*. FIG. 7D is a cross-sectional view of a portion of the cardiac output Doppler catheter of FIGS. 7A, 7B within the circle 7D in FIG. 7B to illustrate the connections of power and ground leads to the transducer 52. Aside from employing additional transducers such as transducer 52 together with the associated leads or wires, the alternative embodiment of FIGS. 7A-7E uses the same components and functions in the same manner as the embodiments of FIGS. 1A through 6B for measuring blood mean velocity.

The advantage of having at least a second transducer that is employed on the side of the Doppler catheter 12 is that this second transducer can be used for measuring a cross-sectional dimension of the artery. This can be done by simply detecting the time of travel of sound waves and its reflection between the second transducer and an adjacent wall of the artery. The distance between the transducer and the artery wall can then be calculated from the time measured and the speed of sound in the blood. If it can be assumed that the Doppler catheter 12 is placed at the central axis of the artery and that the artery has a substantially circular cross-section, then the cross-sectional dimension of the artery can be computed from this time measurement, and from the speed of sound in the blood. If the artery does not have a substantially circular cross-section, employing additional transducers located at different positions around a circumference or perimeter of the Doppler catheter will provide measurement of distances between the Doppler catheter and the artery wall at multiple positions around a circumference or perimeter of the artery to yield multiple (e.g. at least two) cross-sectional dimensions of the artery. Alternatively, instead of using more than one transducer (side transducer) located on the side of Doppler catheter 12, the Doppler catheter 12 may be rotated in the artery so that the only one side transducer is used to measure multiple (e.g. at least two) cross-sectional dimensions of the artery at two or more different angular orientations of the Doppler catheter relative to the artery. More accurate cross-section dimensions of the artery can then be derived from the above measurements.

The ultrasound measurement provided by the Doppler transducer provides the blood mean velocity. Blood volume flow or cardiac output can then be computed from this mean velocity and the cross-sectional dimensions of the artery. Blood pressure monitoring, substance infusion or injection, and retrieval of blood samples in or from the artery can be performed while blood flow is being measured as described above, or when the Doppler catheter is not used for measuring blood flow and the Doppler catheter is not in conduit 14c.

The different embodiments above may be used for measurements and display of information as described in U.S. Pat. No. 5,433,205, which is incorporated herein in its entirety by reference. Sections below are taken from this patent to illustrate how the different embodiments above may be used. FIG. 8 of this document contains the same information as FIG. 1 of U.S. Pat. No. 5,433,205.

FIG. 8 is a schematic view of parts of the body, including the heart 210 and lungs 212. The heart is divided into the right atrium 210a and right ventricle 210b, and the left atrium 210c and left ventricle 210d. The pulmonary artery 214 connects the right ventricle 210b to the lungs 212. The aorta 216 is a passage through which blood goes to the different parts of the body. In a fetus and neonatal patient, the pulmonary artery 214 and aorta 216 are connected by the ductus arteriosus 218.

FIG. 8 shows two positions in which a catheter can be placed into the arteries to determine the blood flow of the patient. Doppler-tipped catheter 220 (which can be any one of the embodiments described above) is positioned down through the heart past the ductus arteriosus in the pulmonary artery 214. Notice that the tip of the Doppler-tipped catheter 220a is near but facing away from the ductus arteriosus 218. Doppler-tipped catheter 222 is placed through the umbilical cord up through the aorta 16 to a position near and facing the ductus arteriosus 218. The velocity of blood in the bloodstream can be determined with the use of a Doppler-tipped catheter in a manner such that the cardiac output or blood flow Q can be computed from the blood mean velocity and the cross-sectional area of the blood vessel. The mean velocity is determined using the Doppler shift in the frequency between the transmitted signal and the received signal. This shift is proportional to the blood velocity.

An important part of monitoring the ventilation perfusion match is monitoring the blood flow in the body. When patients are on life support systems, oxygen is pumped under pressure into the lung 212 at high concentrations. Thus, if the surface area of the lung 212 available for gas exchange is decreased by disease, e.g. pneumonia, the higher concentration of oxygen will provide an adequate amount of oxygen to the body through the available surface area. Sometimes the lung 212 tends to collapse or have poor compliance, as in premature infants. Pressure to deliver the oxygen and open the lungs then becomes essential. However, excess pressure will over-distend the alveoli and squeeze the surrounding blood out, causing an inadequate availability of blood for gas exchange. In this case, due to over-distension, ventilation V is increased; however, due to the squeeze effect, Q is decreased. Catheter 220a will show decreased flow. Conversely, if the pressure is inadequate, the blood supply remains adequate but the gas supply is reduced—normal Q with decreased V. Please note that the concentration of oxygen may be adequate, just that the surface area available for gas exchange is reduced. In the last case, catheter 220a will show normal flow.

Right to left shunting is used loosely with any condition that leads to inadequate oxygenation of the body. Left to right shunting refers to excess blood supply to the lung.

The ductus arteriosus 218 complicates the above picture. If this conduit between the pulmonary artery, the main blood vessel to the lung, and the aorta, the main blood vessel in the body, does not close, the blood takes the path of least resistance and may bypass the lung completely. This effect is caused by excess pressure or over-distension of the lung described above—right to left shunting with V/Q>1. On the other hand, normally the pressure in the aorta is higher than that of the pulmonary artery. Hence, if the ductus is open, the blood will leak back into the lungs—left to right shunting with V/Q<1. Catheter 222a will show retrograde flow and catheter 220a will show increased antegrade flow. This assumes that normal V/Q=1.

The Doppler-tipped catheter placed into an artery of the patient can help determine shunt fractions through the ductus arteriosus 18. The frequency shift signal from the Doppler-tipped catheter will provide the blood flow velocity toward (antegrade) or away from (retrograde) the catheter. The positive portion of the frequency shift signal gives an indication of the antegrade blood flow through the aorta 216 to the body. The negative portion gives an indication of the left-to-right shunting of retrograde blood flow through the ductus arteriosus 218. In this manner, the shunt fraction through the ductus arteriosus 218 can be determined. Alternately, a Doppler-tipped catheter 220 of FIG. 8 will have a retrograde portion of a frequency shift data which corresponds to the blood flow from the right ventricle 210d to the lungs 212, with an antegrade portion which shows the right-to-left shunting through the ductus arteriosus 218. The signal from the velocimeter connected to the catheter can be set to measure blood flow velocity toward (antegrade) or away from (retrograde) the catheter. The software in the computer 224 switches the velocimeter so as to alternately analyze the antegrade and retrograde portion of the signal every 50 milliseconds.

The above sections are essentially taken from U.S. Pat. No. 5,433,205. The artery into which Doppler catheter 12 and 112 may be placed as described above can be the radial, pulmonary, femoral or umbilical artery. Where the artery is an umbilical artery of a neonatal patient, said location for locating the Doppler transducer 12a is close to the patent ductus arteriosus of the patient, and the ultrasound measurement measures antegrade and retrograde blood velocity. The analysis and computations mentioned above may be performed using computer 224 of FIG. 8. As described above, blood pressure may be monitored while Doppler ultrasound measurements are performed. Thus, both the blood velocity (or blood flow in the case of Doppler catheter 112) and information related to the blood pressure measurement may be displayed at substantially the same time on display 226 in FIG. 8, in real time and continuously if desired.

A cardiac assist device 250 may be placed in the aorta 216 as shown in FIG. 8 or the left ventricle 210d (shown as 250' in dashed lines). If placed in the aorta 216, and the catheter 220a is at the position shown in FIG. 8, catheter 220a may be used as shown in FIG. 8 to measure the velocity of the combined blood flow in the aorta and cardiac assist device. If placed in the left ventricle 210d, catheter 220a may be advanced to a location (not shown) in tandem or within cardiac assist device 250' to measure the blood velocity in the cardiac assist device 250'. If the catheter 220a is to be used in this manner, the elongated catheter body of catheter 220a may comprise a material rigid enough to be placed in tandem or within cardiac assist devices, and can contain metal.

A systolic time interval parameter can also be derived from a result of the Doppler measurement described above. For details of such derivation, please see Ahmed et al., "Systolic Time Intervals as Measures of the Contractile State of the Left Ventricular Myocardium in Man," Journal of the American Heart Association, Circulation, Vol. XLVI, September 1972, pp. 559-571.

While the invention has been described above by reference to various embodiments, it will be understood that changes and modifications may be made without departing from the scope of the invention, which is to be defined only by the appended claims and their equivalents.

What is claimed is:

1. A method for measuring blood velocity and derived indices related to blood velocity in an umbilical artery of a neonatal patient, comprising:
    inserting into the umbilical artery an elongated catheter body having a proximal end and a distal end so that the distal end is located at a desired location in the umbilical artery for measuring the blood velocity, said elongated catheter body defining a conduit therein, said desired location being close to a patent ductus arteriosus of the neonatal patient;
    positioning an end of a Doppler catheter near the proximal end of the elongated catheter body, wherein the Doppler catheter includes a Doppler transducer, a wire connected to the Doppler transducer, and a sleeve that provides a sealed environment for the Doppler transducer and the wire when the Doppler transducer and/or the wire is in a first position outside the conduit, when the Doppler transducer is in a second position at said desired location, and when the Doppler transducer is in a position between the first position and the second position;
    thereafter inserting into the conduit, at the proximal end of the elongated catheter body, the Doppler transducer and the wire so that the Doppler transducer passes through, and extends outside, the conduit at the distal end, to be located at said desired location, thereby folding the sleeve;
    performing continuously ultrasound measurement of the blood velocity in the umbilical artery at said desired location using the Doppler transducer to measure antegrade and retrograde blood velocity in the umbilical artery; and
    continuously displaying, in real time, information related to the blood velocity in the umbilical artery.

2. The method of claim 1, further comprising performing blood pressure measurement in the umbilical artery when the ultrasound measurement of the blood using the Doppler transducer is performed.

3. The method of claim 2, further comprising displaying information related to the ultrasound measurement of the blood and information related to the blood pressure measurement at substantially the same time.

4. The method of claim 1, further comprising infusing a substance to the umbilical artery or retrieving a blood sample from the umbilical artery, when the ultrasound measurement of the blood using the Doppler transducer is performed.

5. The method of claim 1, further comprising infusing a substance to the umbilical artery, retrieving a blood sample from the artery, or performing blood pressure measurement in the umbilical artery, when the Doppler transducer and the wire are not in the conduit.

6. The method of claim 1, further comprising conveying ultrasound measurement signals from the Doppler transducer through said wire to an instrument for analysis and display of the signals, wherein the display includes information about systolic time intervals.

7. The method of claim 1, said Doppler catheter further comprising a second transducer and a second wire connected to the second transducer and said method further comprising measuring at least one cross-sectional dimension of the umbilical artery using said second transducer.

8. The method of claim 7, further comprising deriving a blood flow value from measurements of the Doppler transducer and said at least one cross-sectional dimension of the umbilical artery.

9. The method of claim 7, wherein at least two cross-sectional dimensions of the umbilical artery are measured.

10. The method of claim 9, wherein at least two cross-sectional dimensions of the umbilical artery are measured at two different angular orientations of the Doppler transducer relative to the umbilical artery.

11. The method of claim 9, further comprising computing parameters related to blood in arteries, said parameters including a systolic time interval parameter, from a result of measurements of the Doppler transducer.

12. The method of claim 1, said Doppler catheter including a first connector, said method further comprising connecting a second connector attached to the elongated catheter body to the first connector to form a stable connection, wherein the inserting of the Doppler transducer and wire threads the Doppler transducer and a portion of the wire through said conduit and said stable connection until the Doppler transducer emerges at said desired location and outside the conduit at the distal end of said body.

13. A method for measuring blood velocity in an artery, comprising:
    inserting into the artery an elongated catheter body having a proximal end and a distal end so that the distal end is located at a desired location in the artery for measuring the blood velocity, said elongated catheter body defining a conduit therein;
    positioning an end of a Doppler catheter near the proximal end of the elongated catheter body, wherein the Doppler catheter includes a Doppler transducer, a wire connected to the Doppler transducer, and a sleeve that provides a sealed environment for the Doppler transducer and the wire when the Doppler transducer and/or the wire is in a first position outside the conduit, when the Doppler transducer is in a second position at said desired location, and when the Doppler transducer is in a position between the first position and the second position;
    thereafter inserting into the conduit, at the proximal end of the elongated catheter body, the Doppler transducer and the wire so that the Doppler transducer passes through, and extends outside, the conduit at the distal end, to be located at said desired location, thereby folding the sleeve;
    performing continuously ultrasound measurement of the blood velocity in the artery at said desired location using the Doppler transducer; and
    continuously displaying, in real time, information related to blood velocity in the artery and systolic time intervals.

14. The method of claim 13, wherein the artery is an umbilical artery of a neonatal patient, said location being close to a patent ductus arteriosus of the neonatal patient, and the ultrasound measurement measures antegrade and retrograde blood velocity.

15. The method of claim 13, wherein the inserting inserts the elongated catheter body into a radial, pulmonary, femoral or an umbilical artery.

16. The method of claim 13, said Doppler catheter further comprising a second transducer and a second wire connected to the second transducer and said method further comprising measuring at least one cross-sectional dimension of the artery using said second transducer.

17. A method for performing measurements in an artery, comprising:
    inserting into the artery an elongated catheter body having a proximal end and a distal end so that the distal end is located at a desired location in the artery for measuring blood velocity, said elongated catheter body defining a conduit therein;
    positioning an end of a Doppler catheter near the proximal end of the elongated catheter body, wherein the Doppler catheter includes a Doppler transducer, a wire connected to the Doppler transducer, and a sleeve that provides a sealed environment for the Doppler transducer and the wire when the Doppler transducer and/or the wire is in a first position outside the conduit, when the Doppler transducer is in a second position at said desired location, and when the Doppler transducer is in a position between the first position and the second position;
    thereafter inserting into the conduit at the proximal end of the elongated catheter body, the Doppler transducer, a second transducer, wires connected to the Doppler transducer and the second transducer and a first connector so that the Doppler and the second transducers pass through and extend outside the conduit at the distal end, to be located at said desired location, thereby folding the sleeve; and
    performing ultrasound measurement of the blood velocity in the artery and a dimension of the artery at said desired location using the Doppler transducer and the second transducer.

18. The method of claim 17, said Doppler catheter including a first connector, said method further comprising connecting a second connector attached to the elongated catheter body to the first connector to form a stable connection, wherein the inserting of the Doppler transducer and wires threads the Doppler transducer and the second transducer and a portion of the wire through said conduit and said stable connection until the Doppler transducer and the second transducer emerge at said desired location and outside the conduit at the distal end of said elongated catheter body.

19. The method of claim 18, wherein the artery is an umbilical artery of a neonatal patient, said location being close to a patent ductus arteriosus of the patient, and the ultrasound measurement measures antegrade and retrograde blood velocity.

20. The method of claim 18, wherein the inserting inserts the catheter body into a radial, pulmonary, femoral or an umbilical artery.

* * * * *